United States Patent [19]

Cerny

[11] Patent Number: 5,385,561
[45] Date of Patent: Jan. 31, 1995

[54] APPARATUS AND METHOD FOR INJECTING A VISCOUS MATERIAL INTO THE TISSUE OF A PATIENT

[75] Inventor: David E. Cerny, Lilburn, Ga.

[73] Assignee: Bard International, Inc., Murray Hill, N.J.

[21] Appl. No.: 183,172

[22] Filed: Jan. 18, 1994

[51] Int. Cl.$^6$ ............................................. A61M 5/00
[52] U.S. Cl. .................................. 604/264; 604/164; 604/111; 604/274; 128/4
[58] Field of Search .............. 604/264, 164, 165, 274, 604/239, 240, 111, 272; 128/4

[56] References Cited

U.S. PATENT DOCUMENTS

| | | |
|---|---|---|
| 387,454 | 8/1888 | Siegenthaler . |
| 3,662,457 | 5/1972 | Gores . |
| 4,668,226 | 5/1987 | Omata et al. . |
| 4,889,529 | 12/1989 | Haindl . |
| 5,007,940 | 4/1991 | Berg . |
| 5,328,466 | 7/1994 | Demark ........................... 604/111 X |
| 5,336,191 | 8/1994 | Davis et al. ...................... 604/274 X |

OTHER PUBLICATIONS

MicrovasiveProducts for Endourology 1989 Brochure Describing the Williams Cystoscopic Injection Needle.
Cook Urological (1990 1991) Brochure Describing Urological Surgical Products–Fascial Incising Needles and the Williams Cystoscopic Injection Needle.
Van-Tec Incorporated Brochure Describing the Williams Flexible Injection Needle.
Cook Urological Brochure Describing the Amplatz Needle Holder (With Silicone Inserts) and the Willliams Cystoscopic Injection Needle.
Contigen ® Bard ® Collagen Implant Brochure (©1993 C. R. Bard, Inc.).
Stress Incontinence Brochure (©1993 C. R. Bard, Inc.).

Primary Examiner—John D. Yasko
Attorney, Agent, or Firm—Jones & Askew

[57] ABSTRACT

An apparatus and method are disclosed for injecting a viscous material into periurethral tissues as a treatment for urinary incontinence. The apparatus comprises a non-coring needle mounted to the forward end of a catheter. A hub with a luer adapter is fitted to the rearward end of the catheter. To provide the physician with a readily visible indicator of the orientation of the needle orifice, the catheter has a stripe running longitudinally on the catheter in predetermined angular relationship with the needle orifice. Further, the needle hub also has indicia located thereon in predetermined angular relationship with the needle orifice. Thus the physician can ascertain the orientation of the needle orifice through the cystoscope by observing the location of the stripe, or he can determine the orientation of the needle orifice externally by observing the indicia on the needle hub. The physician can therefore maneuver the catheter/needle assembly while noting the angular location of the stripe or hub indicia to position the needle orifice at the optimum orientation for injecting the viscous material.

12 Claims, 4 Drawing Sheets

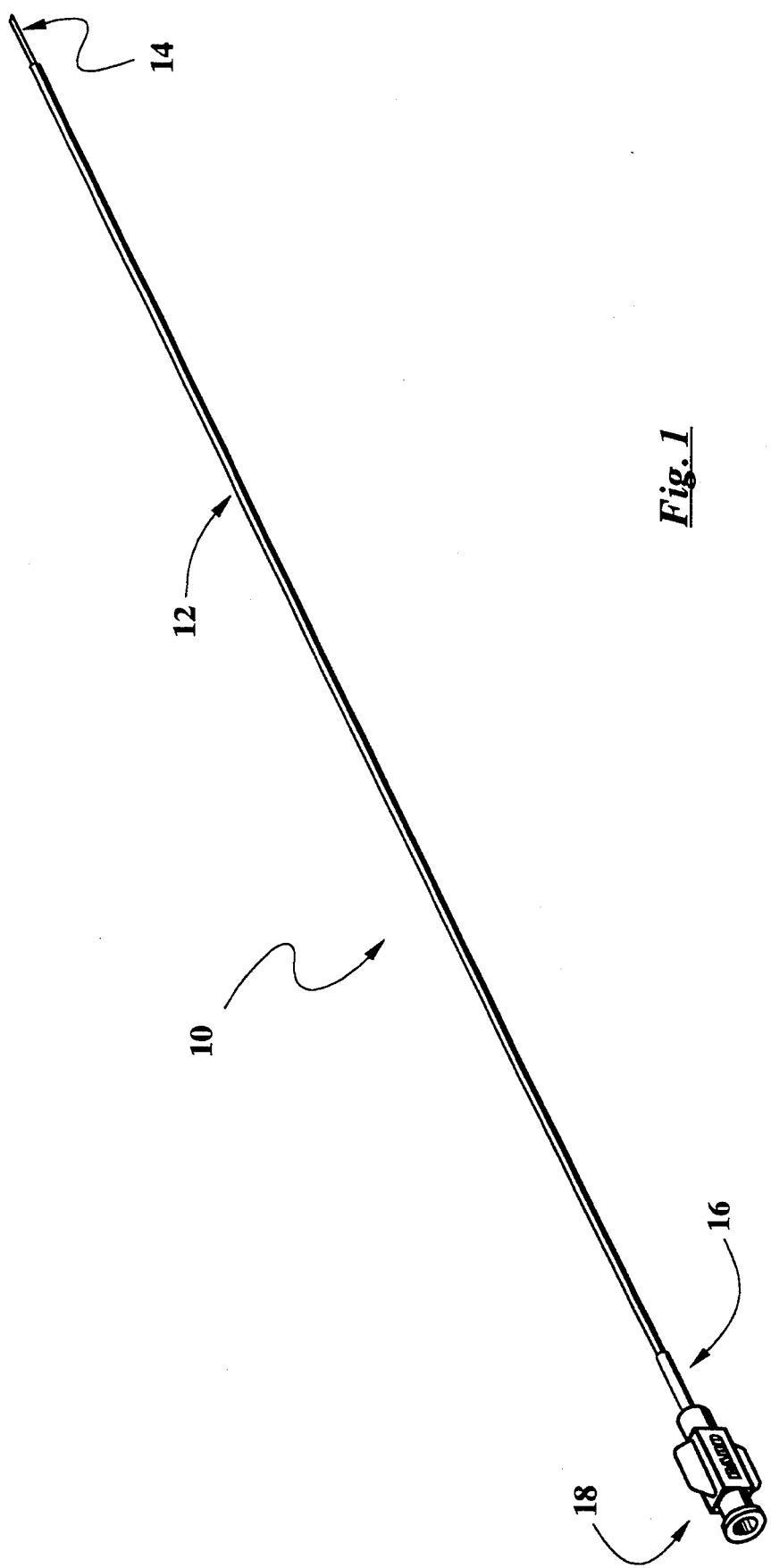

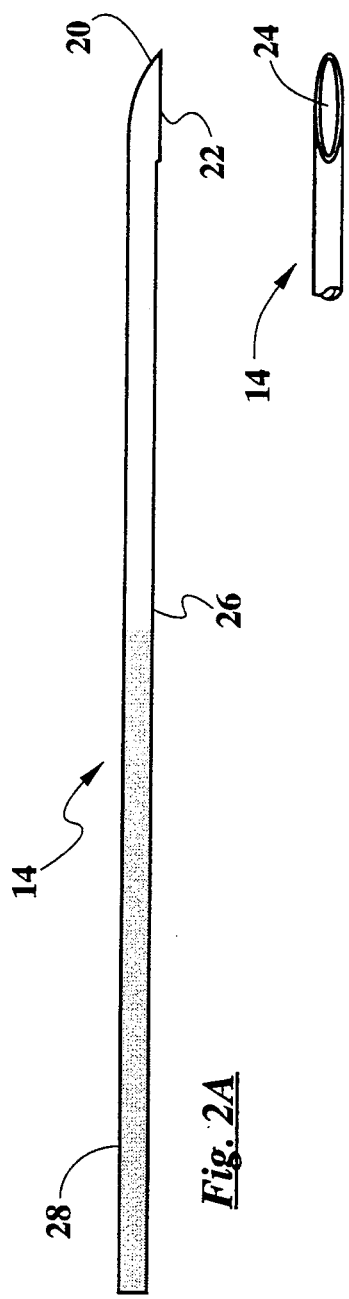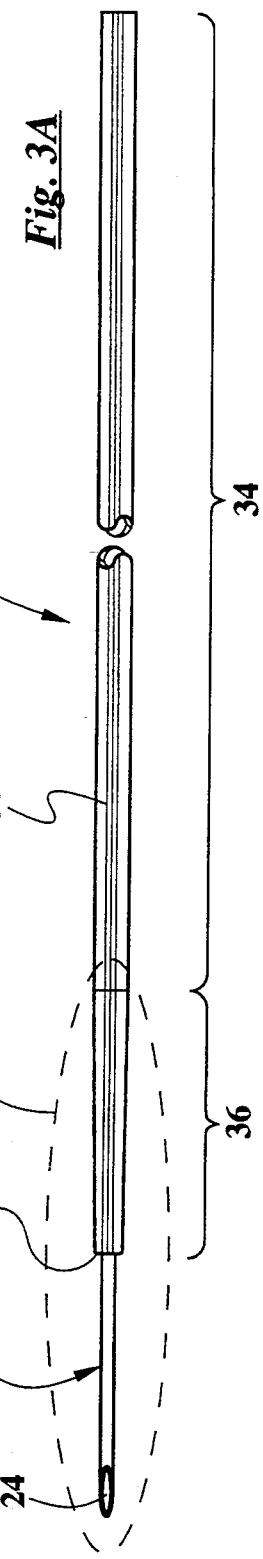

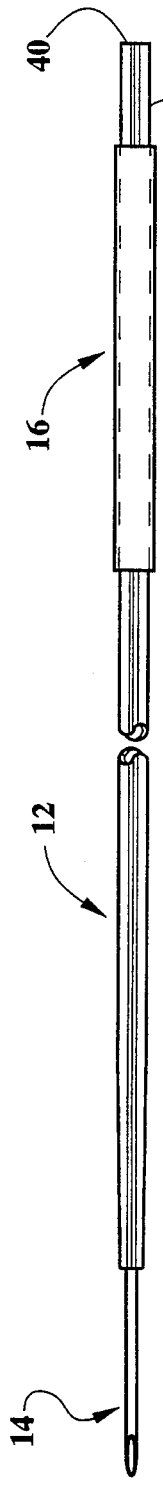
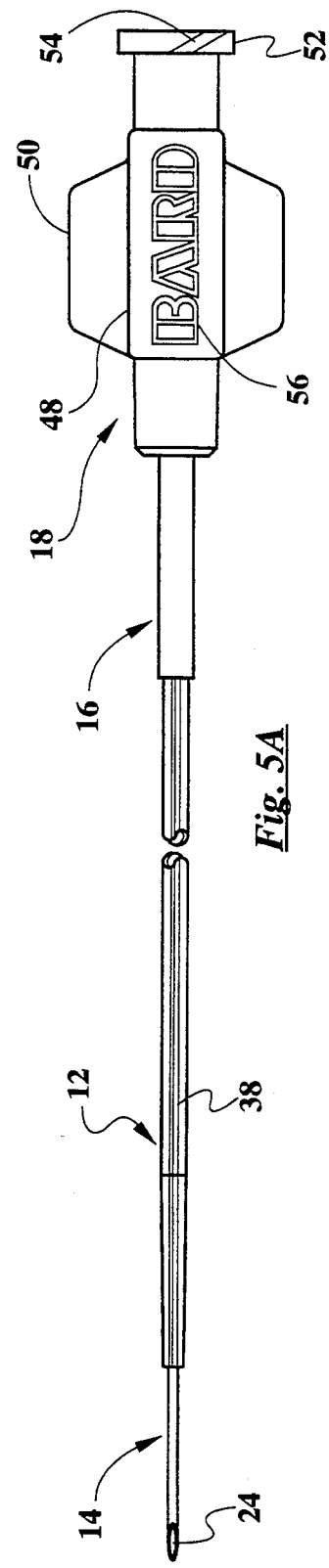
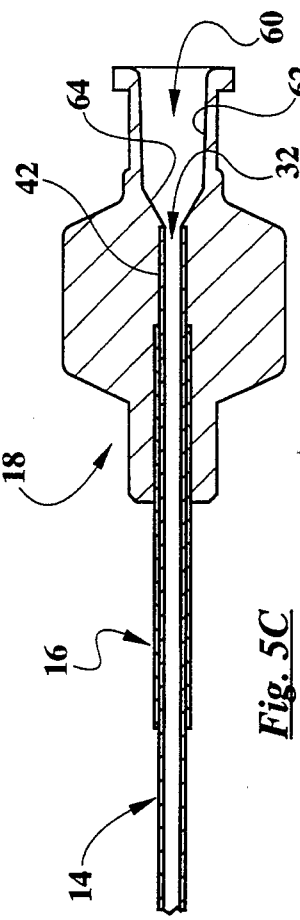
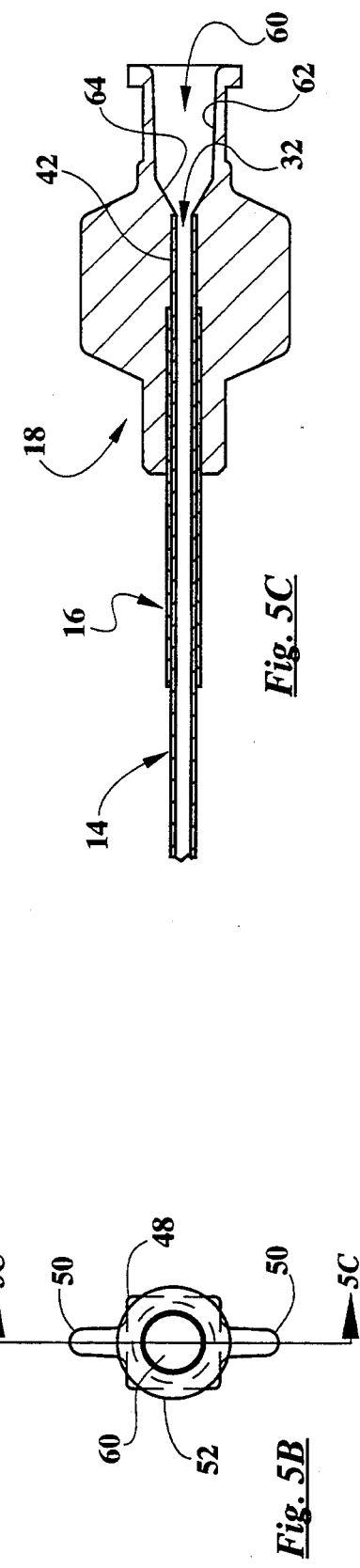
Fig. 4
Fig. 5A
Fig. 5B
Fig. 5C

APPARATUS AND METHOD FOR INJECTING A VISCOUS MATERIAL INTO THE TISSUE OF A PATIENT

TECHNICAL FIELD

The present invention relates generally to medical devices and procedures, and relates more specifically to an apparatus and method for injecting a viscous material into the tissues of a patient. In particular, the invention relates to an apparatus and method for injecting a viscous material such as collagen into the periurethral tissues of a patient as a treatment for urinary incontinence.

BACKGROUND OF THE INVENTION

It is known to treat urinary incontinence by injecting a viscous biocompatible material such as collagen transcystoscopically into the patient's periurethral tissues. The collagen is injected into the submucosal tissues of the urethra and/or bladder neck, and into the tissues adjacent to the urethra. The injection of the collagen creates increased tissue bulk, thereby exerting a coaptive pressure against the urethra. After injection the suspended collagen forms a soft, cohesive network of fibers, and over time the collagen takes on the appearance of normal host tissue.

The collagen can be implanted into the patient either periurethrally or transurethrally. According to the periurethral injection procedure, a needle is advanced through the perineum parallel to the urethra until the needle tip is located in the desired area for injection. Location of the needle tip is verified cystoscopically by observing the movement of adjacent tissue during gentle movement of the needle. When the needle tip is properly positioned, collagen is injected submucosally until tissue bulking closes the lumen across the midline of the urethral opening. The needle is then withdrawn from the initial injection site, and the procedure is repeated at a location directly across the urethra from the initial injection site. Collagen is injected until urethral closure is observed through the cystoscope, or until a maximum of 30 cc of collagen has been injected.

According to the transurethral procedure, a cystoscope is introduced into the patient's urethra. A catheter having a needle at its forward end is advanced through the working channel of the cystoscope to the desired area for injection. The needle is then advanced into the urethral wall, and collagen is injected submucosally until tissue bulking closes the lumen across the midline of the urethral opening. The needle is then withdrawn from the initial injection site and advanced into other locations on the urethral wall as needed. Material is injected at these other locations until urethral coaptation is observed through the cystoscope, or until the maximum of 30 cc of collagen has been injected.

Occasional problems arise in both the periurethral and transurethral injection procedures. On certain occasions it may require injection of an unexpectedly high volume of collagen to attain coaptation. On other occasions, even where coaptation of the urethra is achieved during the procedure, it has been found that on certain occasions within twenty-four to forty-eight hours after the procedure coaptation is not maintained. Additional injections of collagen may then be required to augment the initial injections to reattain coaptation. Such additional injections result in increased patient discomfort, cost, and patient morbidity.

Thus there is a need for an improved apparatus and method for injecting collagen or other suitable viscous biocompatible material into the periurethral tissues as a treatment for urinary incontinence.

There is a further need for an improved apparatus and method for periurethral and transurethral injection of collagen or other suitable viscous biocompatible material which affords coaptation while minimizing the volume of collagen which must be injected.

There is a still further need for an improved apparatus and method for periurethral and transurethral injection of collagen or other suitable viscous biocompatible material which maintains coaptation of the urethra once achieved.

SUMMARY OF THE INVENTION

As will be seen, the present invention overcomes these and other problems associated with prior art apparatus and procedures for treating urinary incontinence by injecting viscous biocompatible material into the periurethral tissues. Stated generally, the present invention provides an improved apparatus and method for injecting collagen or other suitable viscous biocompatible material into the periurethral tissues to increase tissue bulk and thereby exert an occlusive pressure against the urethra. The improved method and apparatus not only attains coaptation of the urethra but significantly enhances the prospects for continued coaptation twenty-four to forty-eight hours after the procedure.

Stated more specifically, it has been found that a significant factor in the loss of urethral coaptation in the period immediately following the injection procedure is the backflow of the injected material through the injection tract.

The viscous injected material does not readily diffuse into the tissues but instead causes the tissues to expand and form a pocket. Although the tissue relaxes over time, the initial resiliency of the tissues can exert enough pressure to force the viscous material to extrude back out through the needle tract. It has been found that a sufficient amount of the viscous injected material can leak back out through the needle tract to require an inordinately high volume of material to attain coaptation. Further, even where coaptation is initially attained, it has been found that on occasion a sufficient amount of the viscous injected material can leak back out through the needle tract to compromise coaptation. In addition, the force of the back flow can cause the needle tract to remain open, thereby delaying the healing process.

The present invention overcomes this problem by providing an apparatus and method which utilizes a non-coring needle, instead of the coring needle conventionally used. The non-coring needle creates a tract which immediately seals and resists backflow of the viscous material. The non-coring needle further allows the tissue to heal more quickly and to retain the injected material in the desired location.

However, the use of a non-coring needle presents further difficulties. Since the orifice of a non-coring needle is essentially on the side of the needle, the viscous material will be injected substantially transversely to the axis of the needle. While lateral injection of the material is not a problem with conventional injectable substances which are readily diffused into the tissues, it poses a significant difficulty when injecting viscous material into the periurethral tissues as a treatment for urinary incontinence. Depending upon the orientation of the needle orifice, the viscous material can be injected toward the urethra, away from the urethra, or laterally. This infusion of the injected material in a transverse direction can cause the viscous material to be injected too far from the urethra to cause coaptation, or so far that an undue amount of injectected material is required to attain coaptation.

To overcome these problems, the present invention comprises a non-coring needle mounted to the forward end of a catheter. A hub with a luer adapter is fitted to the rearward end of the catheter. To provide the physician with a readily visible indicator of the orientation of the needle orifice, the catheter has a stripe running longitudinally on the catheter in predetermined angular relationship with the needle orifice. Further, the needle hub also has indicia located in predetermined angular relationship with the needle orifice. Thus the physician can ascertain the orientation of the needle orifice through the cystoscope by observing the location of the stripe, or he can determine externally the orientation of the needle orifice by observing the indicia on the needle hub. The physician can therefore maneuver the catheter/needle assembly while noting the angular location of the stripe or hub indicia to position the needle orifice at the optimum orientation for injecting the viscous material.

The present invention also comprises a method for injecting a viscous material into the tissues of a patient. An endoscope is inserted into the body of a patient to a point proximate to an injection location. A cannula having a non-coring needle disposed at its forward end is then introduced through the working channel of the endoscope and into the tissues of the patient to a point immediately adjacent the injection location. The non-coring needle has an orifice on one side, and the apparatus includes indicia inscribed thereon in predetermined alignment with the orifice of the needle and visible to the physician when the needle is positioned adjacent the injection location. The orientation of the indicia is observed to determine the orientation of the needle orifice, and the cannula and needle are rotated until the orifice on the needle is aligned toward the injection location. The viscous substance is then injected through the cannula and the needle into the injection location.

In the method of the disclosed embodiment, a procedure for injecting a viscous substance into the periurethral tissues of a patient as a treatment for urinary incontinence is described. According to the method of the disclosed embodiment, a cystoscope is inserted into the body of a patient either periurethrally or transurethrally to a point adjacent an injection site in the periurethral tissues of the patient. The cannula has a stripe inscribed along its length and aligned with the orifice of the non-coring needle. Further, a hub at the rearward end of the cannula has indicia disposed thereon and aligned with the orifice of the non-coring needle. To determine the orientation of the needle orifice, the physician can observe either the stripe on the cannula through the cystoscope or the indicia on the needle hub outside the cystoscope. When the needle has been properly positioned, collagen is injected by a syringe coupled to the rearward end of the cannula through the cannula and needle into the periurethral tissues of the patient in a quantity sufficient to achieve coaptation of the urethra.

Thus it is an object of the present invention to provide an improved apparatus and method for injecting collagen or other suitable viscous biocompatible material into the periurethral tissues as a treatment for urinary incontinence.

It is a further object of the present invention to provide an improved apparatus and method for transcystoscopic injection of collagen or other suitable viscous biocompatible material which maintains coaptation of the urethra once achieved.

Another object of the present invention is to provide an improved apparatus and method for transcystoscopic injection of collagen or other suitable viscous biocompatible material which facilitates rapid healing of the needle tract.

Other objects, features, and advantages of the present invention will become apparent upon reading the following specification, when taken in conjunction with the drawings and the appended claims.

BRIEF DESCRIPTION OF THE DRAWINGS

FIG. 1 is an orthogonal view of an injection needle assembly according to the present invention.

FIG. 2A is a side view of the non-coring needle of the needle assembly of FIG. 1; FIG. 2B is a partial top view of the needle of FIG. 2A.

FIG. 3A is a side view of the non-coring needle of FIGS. 2A-B mounted at the forward end of a catheter; FIG. 3B is an enlarged side cut-away view of the section identified by the dashed oval 3B in FIG. 3A.

FIG. 4 is a side view of the needle and catheter assembly of FIGS. 3A-B having a strain relief sheath mounted to a rearward portion thereof.

FIG. 5A is a side view of the needle, catheter, and strain relief sheath assembly of FIG. 4 mounted to an adapter hub; FIG. 5B is an end view of the apparatus of FIG. 5A: and FIG. 5C is a partial side cut-away view taken along line 5C—5C of FIG. 5B.

DETAILED DESCRIPTION OF THE DISCLOSED EMBODIMENT

Figure 6:
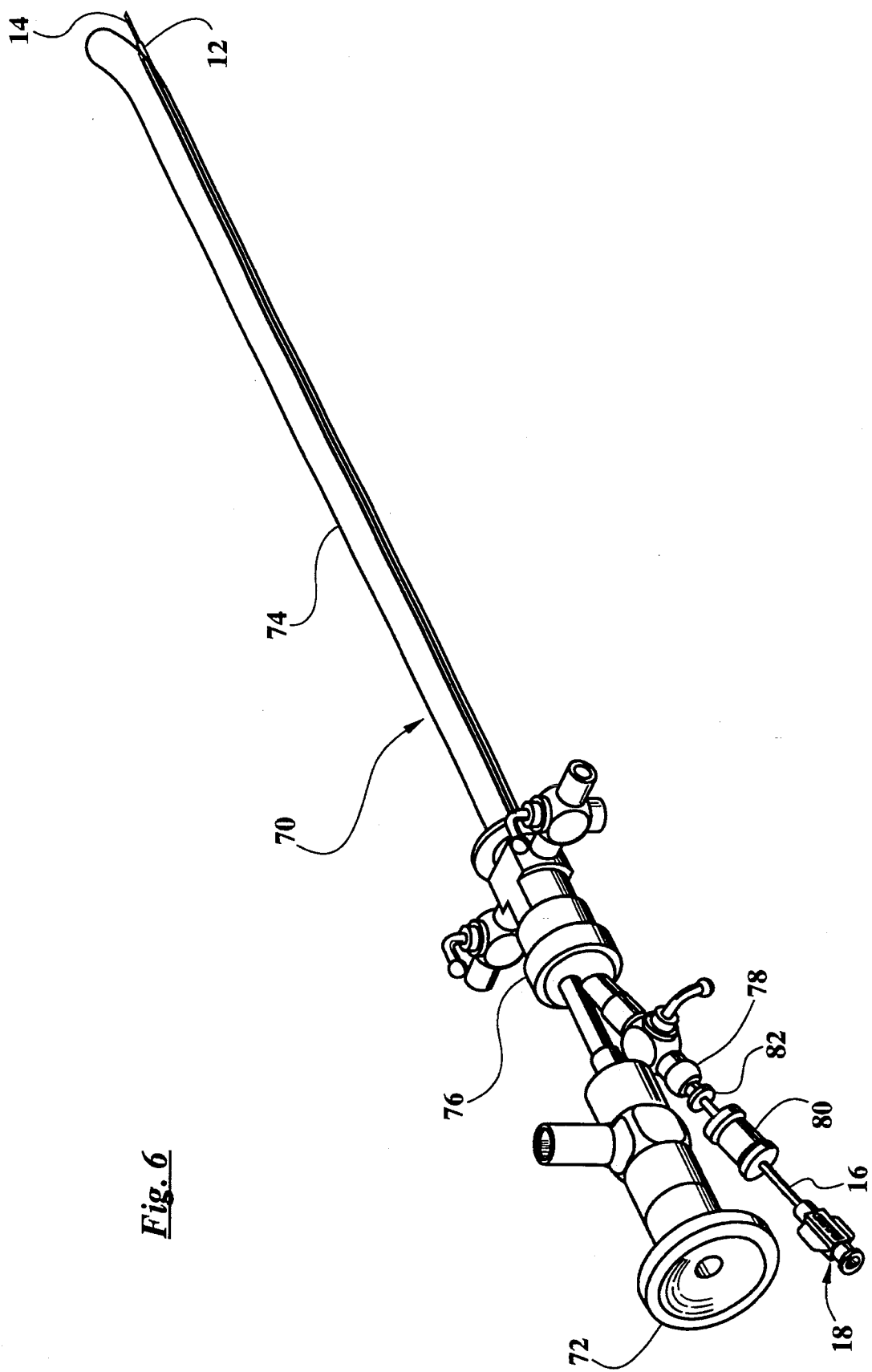
FIG. 6 is an orthogonal view of the needle assembly of FIG. 1 positioned within the working channel of a cystoscope.

Referring now to the drawings, in which like numerals indicate like elements throughout the several views, FIG. 1 shows a cannula assembly 10 according to the present invention. The cannula assembly 10 is comprised of a cannula 12 having a needle 14 mounted to its forward end. A strain relief sheath 16 is mounted about the rearward end of the cannula 12. A hub 18 is molded around the rearward ends of the cannula 12 and strain relief sheath 16. Each of these components will be discussed in more detail below.

Referring now to FIGS. 2A-B, the needle 14 is of a noncoring variety and is comprised of stainless steel. The needle 14 is elongated and has a central longitudinal bore. The needle 14 further has a deflected forward end 20 which reduces or closes the main bevel 22 of the needle to almost zero degrees. An oblong orifice 24 is thus formed on one side 26 of the needle 14. The rearward portion of the needle is grit blasted to provide a roughened surface 28.

Referring now to FIGS. 3A-B, the needle 14 is shown mounted to the forward end 30 of the catheter 12. The catheter 12 is an elongated tubing having a central lumen 32. In the disclosed embodiment the cannula is comprised of a polycarbonate material. A major portion 34 of the catheter 12 is of constant diameter and cross section, while a forward portion 36 is tapered. The inner diameter of the tapered section 36 narrows to intimately surround the roughened portion 28 of the needle 14. The external surface of the cannula 12 has a longitudinal stripe 38 running its entire length along one side thereof. The stripe 38 on the cannula 12 is angularly aligned with the orifice 24 of the needle 14.

FIG. 4 shows the cannula 12 and needle 14 with the strain relief sheath 16 sleeved over the cannula adjacent the rearward end 40 of the cannula. A minor portion 42 of the cannula extends through and rearward of the strain relief sheath 16. The strain relief sheath 16 is comprised of polyether block amide or other suitable thermoplastic elastomer. The combination of the sheath 16 and the cannula 12 is thus a more rigid structure than the cannula 12 alone and provides support to the rearward portion of the cannula against bending forces, while also eliminating any sharp interfaces or stress concentrations between the cannula 12 and the hub 18.

FIG. 5A-C show the hub 18 mounted to the needle/cannula/strain relief sheath sub-assembly. As can perhaps most clearly be seen in FIG. 5C, the hub 18 is insert molded onto both the rearward portion of the strain relief sheath 16 and the exposed rearward portion 42 of the cannula 14 which extends rearwardly of the sheath 16. The hub 18 has a main body portion 48 with wings 50 extending upwardly and downwardly from the main body portion. A luer adapter 52 is formed at the rearward end of the main body portion 48. The outer periphery of the luer adapter 52 includes double start fight hand threads 54 formed 180° C. apart for coupling the hub 18 to a luer fitting. The hub 18 further comprises graphics 56 embossed on a face of the main body portion 48 which is axially aligned with the stripe 38 on the cannula 14.

Referring specifically to FIG. 5C, the hub 18 has a longitudinal bore 60 therewithin in communication with the lumen 32 of the cannula 12. The lateral walls 62 defining the longitudinal bore 60 in the hub 18 are tapered in conformance with ANSI Standard MD70.1. The bore 60 terminates in a conical base 64.

Manufacture of the cannula assembly 10 will now be explained. The cannula 12 is made from a standard catheter tubing of constant diameter. The longitudinal stripe is placed on the tubing during manufacture by coextruding a pigmented polycarbonate with the polycarbonate forming the major portion of the tubing. Alternatively, the stripe can be placed on the tubing by other appropriate secondary process, such as printing.

The striped, constant diameter tubing is then "tipped" in a conventional manner to shape the tapered forward portion 36. According to one manufacturing method, the catheter tubing is tipped by placing into the lumen of the tubing a mandrel having a shape corresponding to the desired configuration of the interior surface of the tapered portion 36. The forward portion of the catheter tubing is then introduced into a die having the desired configuration of the exterior surface of the tapered portion 36. The catheter tubing is subjected to RF energy, which softens the polycarbonate and causes the tubing to assume the shape of the die and mandrel. The tubing is then cut to length, and the roughened portion 28 of the needle 14 is glued into the tapered forward end 30 of the cannula 12 using a suitable medical grade adhesive.

According to a second manufacturing method, the catheter is tipped using the needle instead of a mandrel. The needle is inserted into a bore in the die which permits the roughened portion of the needle to extend into the die cavity. The constant diameter tubing is then advanced over the exposed section of needle and into the die. The catheter tubing is subjected to RF energy, which softens the polycarbonate and causes the tubing to conform to the die and needle. When the tubing has cooled and hardened, the tubing is mechanically bonded to the needle by way of the intimate contact between the roughened surface 28 of the needle and the inner diameter of the tubing. The tubing is then cut to length.

With the needle 14 thus attached to the tapered forward portion 36 of the cannula 12, the strain relief sheath 16 is ready to be installed. The strain relief sheath 16 is comprised of a suitable length of polyether block amide or other suitable thermoplastic elastomer and has an inner diameter which closely conforms to the outer diameter of the cannula 12. The strain relief sheath 16 is tack bonded to the periphery of the catheter 12 with medical grade adhesive to prevent movement during manufacture.

The hub 18 is then insert molded onto the cannula/needle/strain relief sheath subassembly. The rearward end of the strain relief sheath 16 and the exposed portion 42 of the cannula which extends through and rearward of the sheath 16 are introduced into a die. A core pin fits into the back end 40 of the cannula 12 and forms the opening 60 the hub 18, while also preventing plastic from entering the cannula. A quantity of polycarbonate plastic is injected into the die. Since the cannula 12 and hub 18 are both comprised of polycarbonate materials, molecular bonding takes place between the hub and the rearward portion 42 of the cannula.

The manner of use of the cannula assembly 10 of the present invention will now be discussed with reference to FIG. 6. The cannula assembly 10 is used in conjunction with a standard cystoscope 70. The cystoscope 70 includes an optical telescope 72, a cystoscope sheath 74, and a bridge 76 by which the telescope is mounted to the sheath. A working channel 78 extends from a point rearward of the bridge 76 and communicates with the lumen of the cystoscope sheath 74. A working channel cap 80 in the form of a silicone rubber plug is located over the end of the working channel 78. Depending upon the diameter of the working channel 78, a stabilizing cannula 82 may be inserted into the working channel as a bushing to provide a closer fit between the cannula assembly 10 and the working channel, thereby to facilitate maneuvering of the cannula assembly within the working channel.

To inject a viscous substance such as collagen into the periurethral tissues of a patient, a physician introduces the cystoscope 70 into the patient transurethrally to a location adjacent the injection site. A luer-type syringe (not shown) charged with collagen or other suitable viscous substance is mounted to the luer adapter 52 of the hub 18. The needle 14 and cannula 12 are then introduced into the back end of the working channel 78 of the cystoscope 70 and advanced. Advantageously, the physician can grasp the main body portion 48 and wings 50 of the hub 18 to direct the cannula along the working channel and to control the angular orientation of the needle. When the needle 14 exits the forward end of the cystoscope sheath 74, the needle is advanced into the urethral wall under cystoscopic guidance, in the conventional manner.

Since the orifice 24 of the non-coring needle 14 is located on the side of the needle, the physician must orient the needle so that the injected material will exit the needle in the desired lateral direction, e.g., toward the urethra. This step is complicated by the fact that the orifice 24 of the needle 14 is difficult to visualize through the cystoscope 70. Further, once the needle 14 has entered the tissues of the patient, the physician cannot see the orifice 24 to orient the needle. However, the physician can easily visualize the stripe 38 on an exposed length of the cannula 12 through the cystoscope, even when the needle has entered the tissues of the patient. Since the stripe 38 on the cannula 12 is angularly aligned with the orifice 24 of the needle 14, the physician can determine the orientation of the needle orifice by observing the orientation of the stripe on the cannula. The physician then grasps the wings 50 of the hub 18 and rotates the cannula assembly 10 until the stripe 38 is oriented in the desired direction of injection. In this manner the physician can maneuver the cannula assembly 10 into the proper location for injection. The plunger of the syringe can then be depressed to inject the collagen into the tissues of the patient. The physician monitors the procedure through the cystoscope 70 and continues to inject collagen until coaptation of the urethra is achieved.

The graphics 56 embossed on a face of the main body portion 48 provide an additional means for determining the angular orientation of the needle. Since the graphics 56, like the stripe 38, are oriented with the orifice 24 of the needle 14, the physician can observe the hub 18 to determine the orientation of the needle orifice. This method provides the further advantage that since the hub 18 remains exterior to the cystoscope 70, the orientation of the needle orifice 24 can be determined without having to view the cannula assembly through the cystoscope.

As will be appreciated, the utilization of a non-coring needle provides substantial advantages. As the needle 14 penetrates the tissues of the patient, the non-coring tip 20 slits the tissues, rather than coring. When the needle 14 is later withdrawn, the needle tract immediately seals and resists backflow of the injected collagen. The non-coring needle further allows the tissue to heal more quickly and to retain the collagen in the desired location.

While the present invention has been disclosed with respect to a particular embodiment comprising a non-coring needle wherein the bevel surface 22 has substantially a 0° angle with respect to the longitudinal axis of the needle, it will be appreciated that a 0° bevel is not mandatory to achieve a non-coring action. It has been found that bevel surface orientations of up to 5° with respect to the longitudinal axis will resist coring, though such angles will tend to cut a C-shaped flap in the tissues rather than slitting them. However, the C-shaped flap also seals quickly and prevents backflow. As the bevel face orientation increases beyond 5° and approaches 30°, the needle will core with increasing severity, with the disadvantages enumerated above.

While the present invention has been disclosed with respect to the use of a cannula assembly 10 in conjunction with a cystoscope 70 for injecting collagen into the periurethral tissues of a patient as a treatment for urinary incontinence, it will be appreciated that the invention is easily adapted for use with other types of endoscopes, and can be used to inject viscous substances other than collagen, in locations other than the periurethral tissues, for purposes other than treatment of urinary incontinence.

Also, while the present invention has been disclosed with respect to a preferred embodiment 10 which employs a longitudinal stripe 38 on the cannula 12 and graphics 56 embossed on the hub 18 to indicate orientation of the orifice 24 of the needle 14, it will be appreciated that the invention is not limited to a stripe or to embossed graphics, and that different indicia may be placed on the cannula assembly to indicate the orientation of the needle orifice.

Finally, it will be understood that the preferred embodiment has been disclosed by way of example, and that other modifications may occur to those skilled in the art without departing from the scope and spirit of the appended claims.

What is claimed is:

1. A method for injecting a viscous material into the tissues of a patient, comprising the steps of:
   inserting an endoscope having a working channel into the body of a patient to a point proximate to an injection location;
   inserting an apparatus comprising a cannula having a non-coring needle disposed at the forward end thereof through said working channel of said cystoscope and into the tissues of said patient to a point immediately adjacent said injection location, said non-coring needle having an orifice on one side thereof, and said apparatus further comprising indicia inscribed thereon in predetermined alignment with said one side of said non-coring needle upon which said orifice is located, said indicia being visible to said physician when said needle is positioned adjacent said injection location;
   observing the orientation of said indicia to determine the orientation of said needle orifice:
   rotating said cannula and said needle until said orifice on said needle is aligned toward said injection location; and
   injecting a viscous substance through said cannula and said needle into said injection location.

2. The method of claim 1, wherein said indicia is inscribed on said cannula in predetermined alignment with said one side of said non-coring needle upon which said orifice is located, and wherein said step of observing the orientation of said indicia to determine the orientation of said needle orifice comprises the step of observing said indicia on said cannula through said endoscope when said needle positioned adjacent said injection location.

3. The method of claim 2, wherein said indicia on said cannula comprises a stripe placed on said cannula in predetermined alignment with said one side of said non-coring needle upon which said orifice is located, and wherein said step of observing said indicia on said cannula through said endoscope when said needle is positioned adjacent said injection location comprises the step of observing said stripe on said cannula through said endoscope when said needle is positioned adjacent said injection location.

4. The method of claim 1, wherein said apparatus further comprises a needle hub disposed at a rearward end of said cannula, said needle hub remaining outside said patient when said cannula and needle are inserted through said working channel of said endoscope, said needle hub having indicia inscribed thereon in predetermined alignment with said orifice of said needle; and
   wherein said step of observing the orientation of said indicia to determine the orientation of said needle orifice comprises the step of observing said indicia on said needle hub outside said patient.

5. The method of claim 1, wherein said method comprises a method for injecting a viscous material into the periurethral tissues of a patient as a treatment for urinary incontinence;

wherein said step of inserting an endoscope having a working channel into the body of a patient to a point proximate to an injection location comprises the step of inserting a cystoscope having a working channel into the body of a patient to a point proximate to an injection site within the periurethral tissues of said patient; and wherein said step of inserting an apparatus comprising a cannula having a non-coring needle disposed at the forward end thereof through said working channel of said cystoscope and into the tissues of said patient to a point immediately adjacent said injection location comprises inserting said apparatus into the periurethral tissues of said patient.

6. The method of claim 5, wherein said step of inserting a cystoscope into the body of a patient to a point proximate to an injection site within the periurethral tissues of said patient comprises the step of inserting said cystoscope into the body of said patient transurethrally.

7. The method of claim 5, wherein said step of inserting a cystoscope into the body of a patient to a point proximate to an injection site within the periurethral tissues of said patient comprises the step of inserting said cystoscope into the body of said patient periurethrally.

8. The method of claim 1, wherein said step of injecting a viscous substance through said cannula and said needle into said injection location comprises the step of injecting collagen through said cannula and said needle into said injection location.

9. The method of claim 1, wherein said apparatus comprises a fitting disposed at the rearward end of said cannula for coupling said cannula to a syringe, and wherein said step of injecting a viscous substance through said cannula and said needle into said injection location comprises the step of coupling a syringe charged with said viscous substance to the rearward end of said cannula and depressing the plunger of said syringe.

10. An apparatus for injecting a viscous material into the tissues of a patient, comprising:
- a needle having forward and rearward ends, said forward end of said needle including a non-coring tip with an orifice formed on one side of said needle;
- a cannula having forward and rearward ends, said forward end of said cannula being coupled to said rearward end of said needle, said cannula having indicia located thereon in predetermined alignment with said orifice of said needle and disposed such that when said apparatus is inserted through the working channel of an endoscope and the needle advanced into the tissues of a patient, said indicia on said cannula are visible to a physician; and
- a hub coupled to said rearward end of said cannula, said needle hub remaining outside said patient when said cannula and needle are inserted through the working channel of an endoscope, and said hub having indicia located thereon in predetermined alignment with said orifice of said needle:
- whereby when said cannula and needle are inserted through the working channel of an endoscope and said needle is advanced into the tissues of a patient, the orientation of said needle orifice can be determined by observing said indicia on said cannula through said endoscope or by observing said indicia on said hub outside said endoscope.

11. The apparatus of claim 10, wherein said indicia on said cannula comprises a longitudinal stripe marked on said cannula.

12. The apparatus of claim 10, wherein said hub further comprises a fitting for coupling said hub to a syringe.

* * * * *